United States Patent [19]

Dessau

[11] Patent Number: 5,200,375
[45] Date of Patent: Apr. 6, 1993

[54] HYDROGEN REGENERATION OF MONOFUNCTIONAL DEHYDROGENATION AND AROMATIZATION CATALYSTS

[75] Inventor: Ralph M. Dessau, Edison, N.J.
[73] Assignee: Mobil Oil Corporation, Fairfax, Va.
[21] Appl. No.: 819,563
[22] Filed: Jan. 6, 1992

Related U.S. Application Data

[63] Continuation of Ser. No. 597,218, Oct. 15, 1990, abandoned.
[51] Int. Cl.$^5$ .................. B01J 29/38; B01J 38/10; C07C 5/333; C10G 35/095
[52] U.S. Cl. .................. 502/53; 208/140; 585/444; 585/660
[58] Field of Search .................. 502/53, 50

[56] References Cited

U.S. PATENT DOCUMENTS

| | | | |
|---|---|---|---|
| 4,417,083 | 11/1983 | Bernard et al. | 502/53 |
| 4,868,145 | 9/1989 | Dessau et al. | 502/66 |
| 4,886,926 | 12/1989 | Dessau et al. | 585/44 |
| 4,931,416 | 6/1990 | Dessau | 502/74 |

Primary Examiner—Paul E. Konopka
Attorney, Agent, or Firm—Alexander J. McKillop; Malcolm D. Keen; Marina V. Schneller

[57] ABSTRACT

The process is a hydrogen regeneration of spent Group VIII metal modified non-acidic microporous crystalline materials employed as catalysts in dehydrogenation and dehydrocyclization.

14 Claims, 2 Drawing Sheets

HYDROGEN REGENERATION OF MONOFUNCTIONAL DEHYDROGENATION AND AROMATIZATION CATALYSTS

The application is continuation of Ser. No. 07/597,218 filed Oct. 15, 1990 and now abandoned.

FIELD OF THE INVENTION

Non-acidic microporous crystalline materials in combination with platinum group metals, as catalysts, have been found to exhibit high dehydrogenation and dehydrocyclization selectivity under dehydrogenation and dehydrocyclization conditions of paraffins for production of the unsaturated analog of the paraffin. Those catalysts are substantially monofunctional.

The present invention is directed to hydrogen regeneration of aged catalysts. Accordingly, an object of the invention is to substantially recover process activity of dehydrogenation and/or dehydrocyclization of the first cycle, prior to regeneration, in cycle(s) subsequent to regeneration.

Various dehydrogenation products are commercially significant. Isobutylene is one such desirable product which is used as a reactant for the production of alkylate, an oligomer of petroleum refinery $C_3$-$C_4$ off gases, which includes high octane gasoline components, and for the production of methyl-t-butyl ether, when isobutylene is reacted with methanol.

An object of the invention is to provide a dehydrogenation/dehydrocyclization catalyst exhibiting high selectivity in cyclical processes.

Accordingly, an object of the process is to produce unsaturated products with high selectivity.

Another object of the invention is to produce isobutylene product with high selectivity.

BACKGROUND OF THE INVENTION

The term "crystalline" used to refer to these materials relates to the ordered definite crystalline structure of the material which is unique and thus identifiable by a characteristic X-ray diffraction pattern.

The term "microporous" as it refers to such material relates to pores, or channels, with diameters of less than 20 Angstroms. Examples of these microporous crystalline materials include crystalline silicates, crystalline alumino-silicates (zeolites), crystalline ALPOs, crystalline SAPO and related compositions and intercalated pillared materials derived from clays, layered silicates and titanates. The crystalline silicate, alumino silicate (zeolites), ALPOs and SAPOs, have pores of uniform size and channel systems which are uniquely determined by unit structure of the material. The uniform pore size and/or channel systems allow such a material to selectively absorb molecules of certain dimensions and shapes. In the art, microporous material having pores, or channels, of less than 20 Angstroms, can be divided into small, medium and large pore by the diameters of those pores, or channels. The pores of the small pore material have an average diameter of less than 5 Angstroms; medium size pores range from an average diameter of about 5 to about 7 Angstroms, and large pore silicates indicates a diameter of greater than about 7. The word "average" is used to refer to diameter to embrace those species in which the pore is elliptical. Alternatively, the demarcation between small, medium, and large pore materials can be based on the following sorption properties (measured at room temperature for crystallites having a minimum dimension of 0.1 micron):

1. Small pore: n-$C_6$/i-$C_6$ sorption ratio greater than approximately 10.
2. Medium pore: n-$C_6$/i-$C_6$ is less than 10 and n-$C_6$/Mesitylene sorption ratio greater than approximately 5.
3. Large pore: n-$C_6$/Mesitylene sorption ratio less than approximately 5.

In the art, zeolites are a subclass of crystalline microporous silicates. Zeolites can contain aluminum as well as silicon. In some zeolites, the upper limit of the silicon/aluminum atomic ratio is unbounded. ZSM-5 is one such example wherein the silicon/aluminum atomic ratio is at least 2.5 and up to infinity. By way of illustration, U.S. Pat. No. 3,941,871, reissued as RE 29,948, discloses a porous crystalline silicate made from a reaction mixture containing no deliberately added aluminum and exhibiting the X-ray diffraction pattern characteristic of ZSM-5 zeolites; in certain examples tin is deliberately added to the silicate synthesis mixture.

Zeolites can be acidic or non-acidic, depending on the framework aluminum content and on the amount of compensating cations, such as $Na^+$, $K^+$, etc. ALPOs described in U.S. Pat. No. 4,310,440, which is incorporated by reference herein, are neutral. SAPOs described for example in U.S. Pat. No. 4,440,871, which is incorporated by reference herein, can be acidic or non-acidic depending on the ratio of framework Al:P therein and the compensating cation, such as $Na^+$, $K^+$ (other than proton species and other than proton forming species such as $NH^+_4$).

SUMMARY OF THE INVENTION

The process of the invention comprises regenerating a monofunctional dehydrogenation/dehydrocyclization catalyst in hydrogen. The process of the invention comprises aging that non-acidic catalyst in a dehydrogenation and/or dehydrocyclization process, regenerating the aged catalyst under conditions of elevated temperature in the absence of oxygen, and employing the regenerated catalyst in a subsequent cycle of the dehydrogenation and/or dehydrocyclization process. Oxygen (air) regeneration requires high exotherms, which frequently lead to platinum metal migration and agglomeration. Such metal migration and agglomeration can necessitate subsequent metal redispersion via expensive rejuvenation techniques.

It is noted that mild air treatment of these catalysts at 300° to 350° C. for their regeneration restores catalyst activity but with a significant increase in catalyst aging rates following air treatment.

Regeneration, in the absence of oxygen, is particularly effective for monofunctional metal catalysts. In the presence of high pressure hydrogen, metal sites of the monofunctional catalysts appear to catalyze coke removal by hydrogenation. By comparison, dual functional catalysts, such as those containing platinum on an acidic microporous crystalline material generally require air regeneration.

The non-acidic catalyst comprises a platinum group metal, the non-acidic microporous crystalline material, and is monofunctional because of the non-acidic nature; optionally, the non-acidic catalyst comprises a platinum group metal, the non-acidic microporous crystalline material combined with titanium or catalytically inert titania, wherein the amount of titanium and/or catalytically inert titania is effective to decrease the ageing of the non-acidic microporous crystalline material, under said conditions of paraffin dehydrogenation and paraffin dehydrocyclization.

In a preferred embodiment, the composition comprises a microporous crystalline material containing a modifier (such as tin, lead, thallium or indium). It has been discovered that these modifier containing microporous crystalline materials in non-acidic form combined with a dehydrogenation metal exhibit high selectivity for dehydrogenation and/or dehydrocyclization of paraffins, while exhibiting decreased selectivity for cracking.

DESCRIPTION OF THE DRAWING

The FIG. 1 shows the effect of hydrogen regeneration in a graph of a plot of isobutene (production) vs. days on stream.

DETAILED DESCRIPTION OF THE INVENTION

Figure 1:
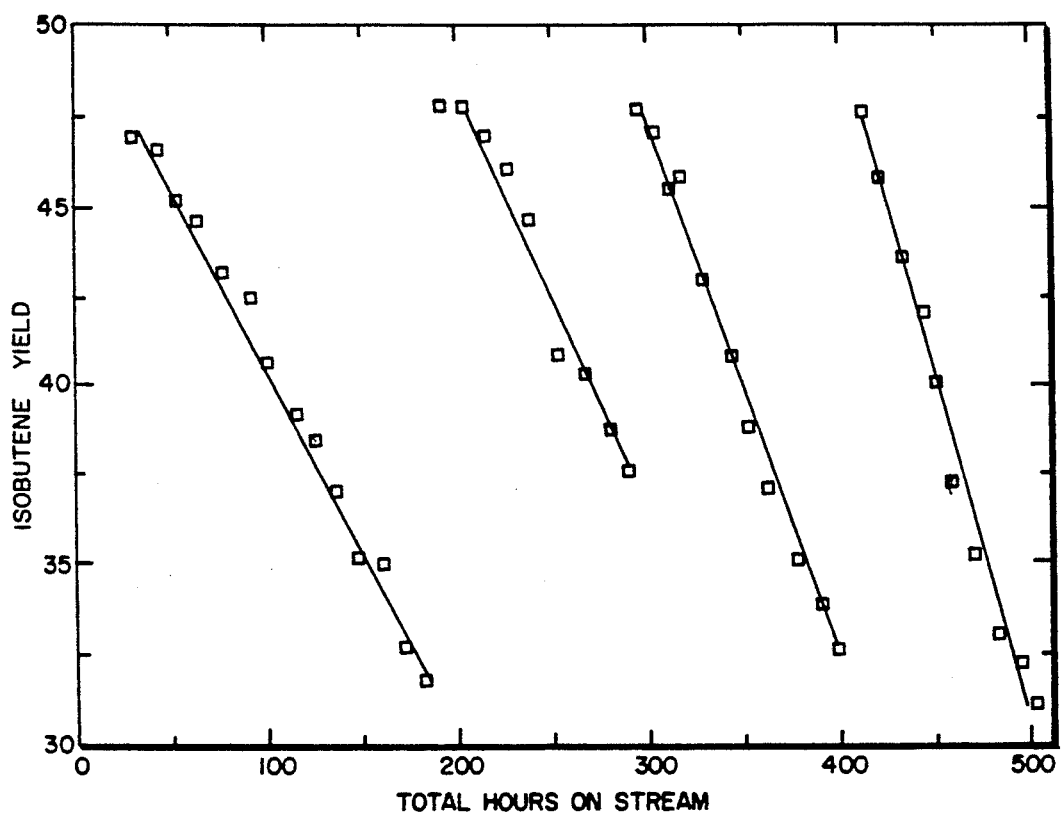

The non-acidic catalyst comprises a hydrogenation/dehydrogenation metal, and a non-acidic microporous crystalline material. Optionally, that monofunctional catalyst may be combined with titanium or catalytically inert titania, wherein the amount of titanium and/or catalytically inert titania is effective to decrease the aging of the non-acidic microporous crystalline material, under dehydrogenation and/or dehydrocyclization conditions, described below. As catalysts these non-acidic forms of compositions exhibit extremely high selectivity for paraffin dehydrogenation and/or dehydrocyclization reactions, under conditions effective for paraffin dehydrogenation and/or aromatization.

The amount of hydrogenation/dehydrogenation metal in the catalyst can range from 0.01 to 30 weight percent and preferably 0.1 to 10 weight percent of the crystalline material. In a preferred embodiment, platinum is the hydrogenation/dehydrogenation metal. However, the hydrogenation/dehydrogenation metal can be any Group VIII metal including those of the platinum group, chromium and vanadium.

The microporous crystalline materials, if acidic as a result of synthesis, can be rendered non-acidic by base exchange to remove acidic functions contained therein. For example, if the microporous crystalline material contains framework aluminum, in the as-synthesized form, the microporous crystalline material can be base exchanged. In this embodiment, base exchange is effected after hydrogenation/dehydrogenation metal incorporation. Base exchange can be with an ionic Group IA metal. The base-exchange can be accomplished by slurring the material in an aqueous solution of suitable Group IA compound such as sodium hydroxide, potassium chloride, cesium hydroxide and the like. The base exchange can be accomplished under selected conditions of reagent concentration, pH, contact time, and the like, so as to eliminate substantially the base-exchangeable acidic content. Such a base-exchanged hydrogenation/dehydrogenation metal containing zeolite is essentially "non-acidic".

In a preferred embodiment the microporous crystalline material is non-acidic, in the sense that it contains substantially no framework aluminum, in the as-synthesized form. In a preferred embodiment, the microporous crystalline material, also contains a modifier selected from the group consisting of tin, lead, thallium or indium. The modifier content of the crystalline microporous materials can range from 0.01 to 20 weight percent. Practically, the modifier content will range from 0.1 to 10 weight percent. These modifier containing microporous crystalline materials are described in U.S. Pat. Nos. 4,886,926; 4,931,416; and 4,868,145, each of which is incorporated by reference herein.

The crystalline microporous modifier containing materials of the invention are characterized by Si/Al ratios of at least 2. However, the silica:alumina ratio of the zeolite can be up to 1000, or greater. In a preferred embodiment the aluminum content of these materials is less than 0.1 weight percent and more preferably less than 0.02 weight percent.

The crystalline microporous modifier-containing or modifier-free material of the invention can contain other elements including boron, iron, chromium, gallium, iridium, ruthenium and rhenium. The content of these other elements in the crystalline microporous silicates can range from 0 to 1? weight percent.

The modifier containing crystalline materials, described herein, are crystalline in the sense that they are identifiable as isostructural with zeolites by X-ray powder diffraction pattern.

The crystalline microporous containing material has an X-ray diffraction pattern which corresponds to a zeolite, SAPO, ALPO, etc.

In a preferred embodiment the pore size of the microporous crystalline containing silicates ranges from about 5 to about 8 Angstroms. Preferably, the silicates exhibit X-ray diffraction patterns of zeolites which are characterized by Constraint Index of 1 to 12.

The method by which Constraint Index is determined is described fully in U.S. Pat. No. 4,016,218, incorporated herein by reference for details of the method. Constraint Index (CI) values for some typical zeolites including some which are suitable as catalysts in the process of this invention are:

| CI (at test temperature) | |
|---|---|
| ZSM-4 | 0.5 (316° C.) |
| ZSM-5 | 6–8.3 (371° C.–316° C.) |
| ZSM-11 | 5–8.7 (371° C.–316° C. |
| ZSM-12 | 2.3 (316° C.) |
| ZSM-20 | 0.5 (371° C.) |
| ZSM-22 | 7.3 (427° C.) |
| ZSM-23 | 9.1 (427° C.) |
| ZSM-34 | 50 (371° C.) |
| ZSM-35 | 4.5 (454° C.) |
| ZSM-48 | 3.5 (538° C.) |
| ZSM-50 | 2.1 (427° C.) |
| MCM-22 | 1.5 (454° C.) |
| TMA Offretite | 3.7 (316° C.) |
| TEA Mordenite | 0.4 (316° C.) |
| Clinoptilolite | 3.4 (510° C.) |
| Mordenite | 0.5 (316° C.) |
| REY | 0.4 (316° C.) |
| Amorphous Silica-alumina | 0.6 (538° C.) |
| Dealuminized Y | 0.5 (510° C.) |
| Erionite | 38 (316° C.) |
| Zeolite Beta | 0.6–2.0 (316° C.–399° C.) |

The above-described Constraint Index is an important and even critical definition of those zeolites which are useful in the process of the present invention. The very nature of this parameter and the above-referenced procedure by which it is determined, however, admits of the possibility that a given zeolite can be tested under somewhat different conditions and thereby exhibit different Constraint Indices. Constraint Index appears to vary somewhat with the severity of the conversion operation and the presence or absence of binder material. Similarly, other variables such as crystal size of the zeolite, the presence of occluded contaminants, etc., may affect the observed Constraint Index value. It will therefore be appreciated that it may be possible to select test conditions, e.g. temperature, as to establish more than one value for the Constraint Index of a particular zeolite. This explains the range of Constraint Indices for some zeolites, such as ZSM-5, ZSM-11 and Beta.

It is to be realized that the above CI values typically characterize the specified zeolites but that such are the cumulative result of several variables useful in the determination and calculation thereof. Thus, for a given zeolite exhibiting a CI value within the range of 5 or less, depending on the temperature employed during the test method within the range of 290° C. to about 538° C., with accompanying conversion between 10% and 60%, the CI may vary within the indicated range of 5 or less. Accordingly, it will be understood to those skilled in the art that the CI as utilized herein, while affording a highly useful means for characterizing the zeolites of interest, is approximately taking into consideration the manner of its determination including the possibility in some instances of compounding variable extremes. However, in all instances, at a temperature within the above-specified range of 290° C. to about 538° C., the CI will have a value for any given zeolite of interest herein of not greater than about 5 and preferably not greater than about 3.

In a preferred embodiment the microporous crystalline material containing tin exhibits the structure of ZSM-5, by X-ray diffraction pattern. The X-ray diffraction pattern of ZSM-5 has been described in U.S. Pat. No. 3,702,886 and RE 29,948 each of which is incorporated by reference herein.

The compositions comprising hydrogenation/dehydrogenation metal combined with the crystalline tin containing silicates do not exhibit any appreciable acid activity. These catalysts would meet the criteria of non-acidic catalysts described by Davis and Venuto, J. CATAL. Vol. 15, p.363 (1969 . Thus, a non-equilibrium mixture of xylenes are formed from either n-octane or each individual methylheptane isomer, with the octane yielding more o-xylene and 2-methyl-heptane yielding mostly m-xylene, at conversions between 10 and 60%.

When, as in embodiments herein, the crystalline tin dehydrogenation metal containing material exhibits an X-ray diffraction pattern of a zeolite, at least some of the dehydrogenation metal may be intrazeolitic, that is, some of that metal is within the pore structure of the crystal, although some of that metal can be on the surface of the crystal. A test for determining whether, for example, Pt is intrazeolitic or extrazeolitic in the case of ZSM-5 is reported by R. M. Dessau, J. CATAL. Vol. 89, p. 520 (1984). The test is based on the selective hydrogenation of olefins.

In accordance with the invention, the compositions of the invention may, optionally, contain titanium or catalytically inert titania. Such compositions exhibit high selectivity for dehydrogenation. The titanium, expressed as $TiO_2$, or catalytically inert titania can be present in amounts ranging from 10 to 99 weight percent of the catalyst composition. The catalytically inert titanium source may be admixed directly with the microporous crystalline material prior to noble metal incorporation or the catalytically inert titanium source may be admixed with the microporous crystalline material after noble metal incorporation.

Compositions of the invention used in catalysis decrease the hydrogen content of the reactant to produce a product having the same number of carbon atoms as the number of carbon atoms in the reactant. By comparison, acidic counterparts of those compositions catalyzed also cracking of paraffins, as a major competing side reaction; and, accordingly, the latter compositions exhibit decreased selectivity for the aromatization of paraffins but increased selectivity for $C_1$-$C_5$ paraffin production.

In a preferred embodiment, the non-acidic crystalline microporous silicates of the invention are treated with $Pt(NH_3)_4Cl_2$ in aqueous solution which has a pH of at least about 7 to incorporate the necessary platinum for catalyst composition formulation.

The non-acidic, crystalline, microporous, dehydrogenation metal containing materials of the invention can be combined with a matrix or binder material to render them attrition resistant and more resistant to the severity of the conditions to which they will be exposed during use in hydrocarbon conversion applications. The combined compositions can contain 1 to 99 weight percent of the materials of the invention based on the combined weight of the matrix (binder) and material of the invention. When used in dehydrogenation and/or dehydrocyclization, the material of the invention will preferably be combined with non-acidic matrix or binder materials. A preferred matrix or binder material would be silica, when the materials of the invention are used in dehydrogenation/hydrogenation or dehydrocyclization. Inactive materials suitably serve as diluents to control the amount of conversion in a given process so that products can be obtained economically and orderly without employing other means for controlling the rate of reaction. These materials may be incorporated into naturally occurring clays, e.g. bentonite and kaolin, to improve the crush strength of the catalyst under commercial operating conditions. Said materials, i.e. clays, oxides, etc., function as binders for the catalyst. It may be desirable to provide a catalyst having good crush strength because in commercial use it is desirable to prevent the catalyst from breaking down into powder-like materials. These clay binders have been employed normally only for the purpose of improving the crush strength of the overall catalyst.

Naturally occurring clays which can be composited with the new crystal include the montmorillonite and kaolin families which include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification. Binders useful for compositing with the present crystal also include inorganic oxides, notably alumina.

In addition to the foregoing materials, the crystalline material can be composited with a porous matrix material such as silica-alumina, silica-magnesia, silica-zirconia, silica-thoria, silica-beryllia, silica-titania we well as ternary compositions such as silica-alumina-thoria, silica-alumina-zirconia silica-alumina-magnesia and silica-magnesia-zirconia. The relative proportions of finely divided crystalline material and inorganic oxide gel matrix vary widely, with the crystal content ranging from about 1 to about 90 percent by weight and more usually, particularly when the composite is prepared in the form of beads, in the range of about 2 to about 80 weight percent of the composite.

The compositions of the invention exhibit high selectivity for dehydrogenation and/or dehydrocyclization which is evidenced by the examples.

Catalytic Dehydrogenation and Dehydrocyclization

In accordance with the invention catalytic dehydrogenation comprises contacting an aliphatic, with the catalyst composition of the invention to produce the corresponding unsaturated analog together with $H_2$.

In dehydrogenation the feedstocks comprise at least one unsubstituted or substituted straight or branched chain aliphatic compound in which the aliphatic moiety has two to five carbon atoms. In accordance with the invention, dehydrogenation of the aliphatic moiety occurs to yield the unsaturated analog. When the aliphatic moiety is substituted, the substituents can be aryls substituted or unsubstituted. The class of reactants includes alkanes of 2 to 5 carbon atoms, such as ethane, propane, butane, isobutane, pentane and 2-methylbutane. Dehydrogenation of those respective alkane reactants will yield ethylene, propylene, butene, isobutene, pentene and isopentene.

The class of reactants includes olefins of 2 to 5 carbon atoms such as ethylene, butene, isobutene, pentene, and isopentene. Dehydrogenation of ethylene will produce acetylene; dehydrogenation of butene will produce butadiene and dehydrogenation of isopentene will produce isoprene.

The class of reactants employed in the dehydrogenation of the invention includes aromatic substituted aliphatics, aryl substituted aliphatics. Preferably, the aliphatic group of the aryl substituted aliphatic contains less than four carbon atoms and more preferably more than 1 carbon atom. The aryl substituted aliphatic reactants embrace unsubstituted arylaliphatics and alkyl substituted aryl aliphatics and; similarly, each of the alkyls of said alkyl substituted alkylaryls contains preferably less than 4 carbon atoms. By way of illustration reactants such as ethyl benzene, diethylbenzene, ethyl toluene, and cumene are representative of these compounds. On dehydrogenation in accordance with the invention, ethyl benzene will produce styrene; ethyl toluene will produce methylstyrene; cumene, isopropenylbenzene; and diethylbenzene, divinylbenzene.

In accordance with the invention, catalytic dehydrogenation conditions include pressures varying from subatmospheric, to atmospheric to greater than atmospheric. Preferred pressures range from 0.1 atmospheres to atmospheric. However, pressures up to 500 psig can be employed. The dehydrogenation is conducted at elevated temperatures ranging from 400° C. to 700° C. and most preferably from 300° C. to 600° C. Reactor inlet $H_2$/feed ratios are 5 or less; even at reactor inlet ratios of zero (0), there will be a hydrogen partial pressure in the reactor because hydrogen is a bi-product of dehydrogenation. The liquid hourly space velocity is 0.1 to 50, preferably 0.5 to 10.

Dehydrogenation may be conducted in the presence or absence of purposefully added hydrogen and in the presence of diluents inert to conditions of the catalytic dehydrogenation such as nitrogen and methane. In particular, dehydrogenation can be advantageously conducted at low hydrogen pressure.

Dehydrocyclization in accordance with the invention comprises contacting an aliphatic of at least six (6) carbon atoms with the catalytic composition comprising a dehydrogenation/hydrogenation metal which can be any Group VIII metal, preferably platinum.

In accordance with the invention, catalytic dehydrocyclization conditions include pressures varying from subatmospheric, to atmospheric to greater than atmospheric. Preferred pressures range from 0.1 atmospheres to atmospheric. However, pressures up to 500 psig can be employed. The dehydrocyclization is conducted at elevated temperatures ranging from 400° C. to 700° C. and most preferably from 300° C. to 600° C. Reactor inlet $H_2$/feed ratios are 5 or less; even at reactor inlet ratios of zero (0), there will be a hydrogen partial pressure in the reactor because hydrogen is a bi-product of dehydrogenation and dehydrocyclization. The liquid hourly space velocity is 0.1 to 50, preferably 0.5 to 10.

The feedstock charge(s) to the new process can be those which are feedstocks for reforming, such as straightrun, thermal, or hydrocracker naphtha. Preferably, for high increases in the aromatic content and high octane numbers of the reformate, the charge to the reformer is a naphtha rich in $C_6$ and $C_7$ paraffins; these are generally difficult to reform selectively using conventional catalysts (such as chlorided Pt-alumina). Naphthas can be obtained by separating the charge into two fractions: a light naphtha and a heavy naphtha. Conventionally such separation is by distillation. The boiling range of the light naphtha is from about 80° F. to about 250° F. and the boiling range of the heavy naphtha will be from 250° F. up to about 450° F. The naphtha will be rich in $C_6$–$C_{10}$ paraffins, and specifically $C_6$ and $C_7$ paraffins. In accordance with one embodiment when the light naphtha is reformed in accordance with the invention, the heavy naphtha will be processed by conventional reforming. The naphtha fractions may be hydrotreated prior to reforming; but hydrotreating is not necessarily required when using the catalyst in accordance with the invention. Initial hydrotreating of a hydrocarbon feed serves to convert sulfur, nitrogen and oxygen derivatives of hydrocarbon to hydrogen sulfide, ammonia, and water while depositing metal contaminant from hydrodecomposition of any organo-metal compounds. Where desired, interstage processing of the effluent from the hydrotreating zone may be effected. Such interstage processing may be undertaken, for example, to provide additional hydrogen, to add or remove heat or to withdraw a portion of the hydrotreated stream for treatment which need not be reformed. Hydrotreating of the heavy naphtha fraction may be essential, prior to reforming in a conventional reforming process. Suitably, the temperature in the hydrotreating catalyst bed will be within the approximate range of 550° F. to 850° F. The feed is conducted through the bed at an overall space velocity between about 0.1 and about 10 and preferably between 0.2 and about 2, with hydrogen initially present in the hydrotreating zone in an amount between about 1000 and 10,000 standard cubic feet per barrel of feed, corresponding to a ratio of between about 2.4 and about 24 moles of hydrogen per mole of hydrocarbon. The catalyst may be any of the known hydrotreating catalysts.

These include Group VIB metals such as molybdenum, chromium and tungsten and Group VIII metals include nickel, cobalt, palladium and platinum. These metal components are deposited, in the form of metals or metal oxides, on the indicated supports in amounts generally between about 0.1 and about 20 weight percent. One particularly useful hydrotreating catalyst is a commercial catalyst known as Chevron ICR 106 which is a nickel-tungsten-alumina-silica-titania catalyst.

When dehydrogenation, dehydrocyclization or reforming is undertaken over the catalyst in accordance with the invention, the temperature can range broadly from 800° F. to 1100° F., generally being greater than about 900° F., preferably being 900° F. (482° C.) to 1050° F.; the pressure will be from about 0 psig to 500 psig, preferably from 0 psig to 250 psig; inlet $H_2$/hydrocarbon can be 5 or less, even zero (0) (because of hydrogen production during reforming, there will be a hydrogen partial pressure in the unit); while the LHSV (liquid hourly space velocity) can be 0.1 to 20, preferably 0.1 to 10.

Regeneration of the aged non-acidic microporous crystalline materials in combination with platinum group metals, in the absence of oxygen provides a catalyst, which exhibits high dehydrogenation and dehydrocyclization selectivity under dehydrogenation and dehydrocyclization conditions of paraffins in second and subsequent cycles of dehydrogenation and/or dehydrocyclization. Regeneration is undertaken at elevated temperatures and pressures, in a hydrogen atmosphere. Regeneration is undertaken when due to aging the yield and/or selectivity of olefin and/or aromatic product falls off under the dehydrogenation and/or dehydrocyclization conditions. Regeneration in accordance with the invention involves passing hydrogen over the aged catalyst, to maintain a hydrogen atmosphere, at elevated pressure over a programmed temperature increase. The pressure may be maintained from at least about 20 psig to 600 psig. The aged catalyst is subjected to elevated temperature from above ambient to a temperature up to 600° C., preferably from 100° C. to 600° C., and most preferably from 300° to 600° C. The time duration can range from 0.5 to 24 hours or more.

EXAMPLES

Example A

In the following experiments, isobutane dehydrogenation reactions were conducted using 0.75 g of 14/30 mesh catalyst in a stainless steel reactor at atmospheric pressure, in the absence of added hydrogen. The external furnace temperature was 554° C. 535° C. for the silica-bound catalyst); weight hourly space velocities were 4.8 and 8.7. Reactor effluents were monitored by on-line gas chromatography.

A non-acidic Pt/Sn-ZSM-5 catalyst, containing 0.43% Pt, 1.03% Sn, 0.67% Na, and only 56 ppm Al, was used to dehydrogenate isobutane to isobutene. The reaction was conducted at 554° C. (oven temperature), 4.8 WHSV, in the absence of added hydrogen, and at atmospheric pressure. An isobutene yield of about 47% was obtained initially; however, the yield dropped gradually over a period of several days to below 35%.

After eight days on stream, the catalyst was regenerated in flowing hydrogen at 400 psig by heating at 1° C./minute to 540° C., where it was held for 6 hours. The reaction was then resumed, and an isobutene yield of 47% was regained.

Catalyst aging was again observed, with the yield dropping to 37% after 5 days.

The catalyst was hydrogen-regenerated a second time at 450° C. and again full activity was restored. The isobutene yield ranged from 48% to 33% after 4.5 days on stream.

The catalyst was then subjected to a third regeneration, which again restored full catalyst activity. Dehydrogenation selectivity was as good or better than that observed over the fresh catalyst. The effect of these hydrogen regenerations is shown graphically in FIG. 1 below:

The aging rates of the regenerated catalysts appeared to be greater than that of the fresh catalyst, with the triply regenerated catalyst aging at about twice the rate of the fresh catalyst.

Example B

Figure 2:
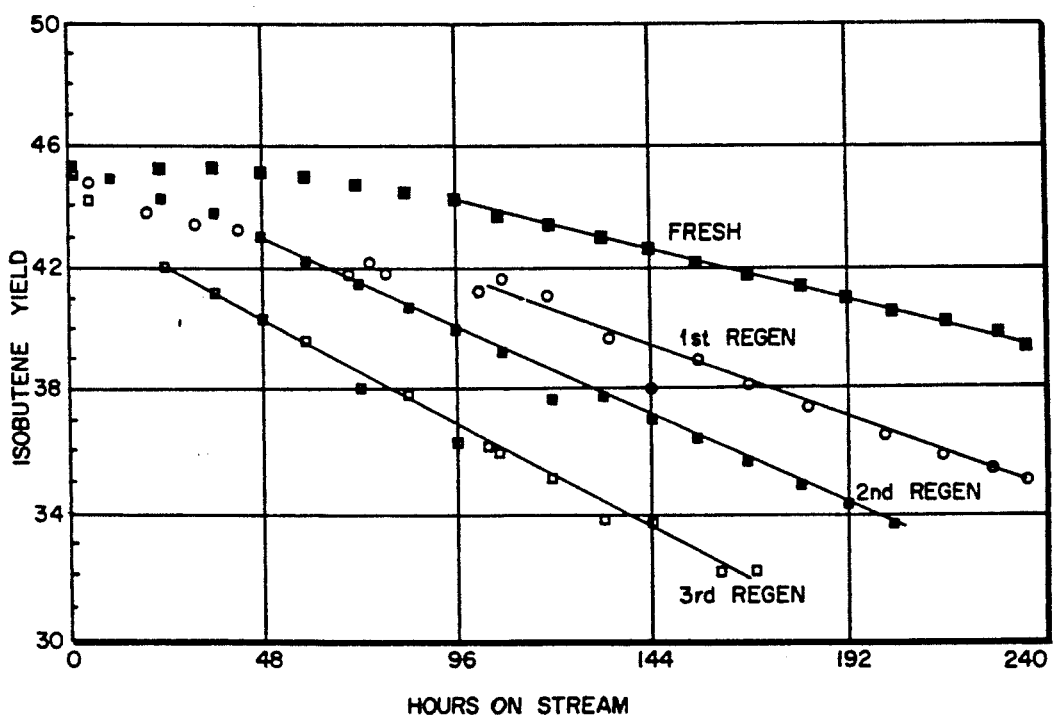
FIG. 2 shows the effect of hydrogen regeneration in a graph of a plot of isobutylene vs hours on stream.

A second set of hydrogen reactivations were performed on a more stable 0.65% Pt/1.0% Sn-ZSM-5 catalyst (one that was air treated at 350° C. rather than at 500° C.). Hydrogen regeneration at 400 psig was now done at 450° C. As this catalyst was more active, isobutane dehydrogenation was studied at 8.7 WHSV. The effect of three hydrogen regenerations is shown graphically in FIG. 2 below:

Example C

Isobutane dehydrogenation was also investigated over an iridium-impregnated 35% silica-bound Pt/Sn-ZSM-5 catalyst. The reaction was conducted at 535° C. and 4.8 WHSV in the absence of added hydrogen. Fairly stable operation was observed under these conditions, with the yield of isobutene declining gradually from 39% to 33% over a period of 7 weeks. The aging rate corresponded to an isobutene yield loss of 0.11% per day.

After seven weeks, this catalyst was regenerated in 400 psig hydrogen at 450° C. for 16 hours, and then restreamed. Full activity was restored; however, the aging rate appeared to double for the first two weeks on stream. Surprisingly, however, the aging rate decreased dramatically after that, with no discernible aging occurring over a period of four weeks. At 45 days on stream, the hydrogen-regenerated catalyst produced comparable isobutane yields to that obtained over the fresh catalyst.

What is claimed is:

1. A process for regenerating a coked monofunctional catalyst composition resulting from catalysis in dehydrogenation and/or dehydrocyclization, wherein the coked monofunctional catalyst composition comprises a dehydrogenation/hydrogenation metal and a non-acidic microporous crystalline material wherein the dehydrogenation/hydrogenation metal is present in an amount which ranges from 0.1 to 20 weight percent;

wherein said material contains 0.1 to 20 weight percent of tin, indium, thallium or lead;

which coked monofunctional catalyst composition suffers dehydrogenation/hydrogenation metal migration and agglomeration, on exposure to oxygen regeneration conditions; wherein the microporous crystalline material has an X-ray diffraction pattern of a zeolite which is selected from the group consisting of ZSM-5, ZSM-11, ZSM-12, ZSM-22, ZSM-23, ZSM-35, ZSM-48 and ZSM-50;

wherein the process consists essentially of:

regenerating the catalyst, in the absence of oxygen, by contacting said catalyst with hydrogen, at an elevated pressure of at least about 400 to about 600 psig and subjecting the catalyst to an elevated temperature of from 100° up to about 600° C.

2. The process of claim 1, wherein the contacting is undertaken for a period of time which can range from 0.5 to 24 hours or more.

3. The process of claim 1, wherein the dehydrogenation/hydrogenation metal is a Group VIII metal.

4. The process of claim 1, wherein the dehydrogenation/hydrogenation metal is platinum.

5. The process of claim 1, wherein the coked monofunctional catalyst composition further contains iridium, ruthenium or rhenium in an amount up to 10 weight percent.

6. The process of claim 1, wherein the catalyst is supported on a binder or matrix material.

7. The process of claim 6, wherein the binder or matrix material is silica.

8. The process of claim 1, wherein the microporous crystalline material exhibits the x-ray diffraction pattern of ZSM-5.

9. The process of claim 8, wherein the dehydrogenation/hydrogenation metal is a Group VIII metal.

10. The process of claim 9, wherein the dehydrogenation/hydrogenation metal is platinum.

11. The process of claim 8, wherein the dehydrogenation/hydrogenation metal is a Group VIII metal.

12. The process of claim 11, wherein the dehydrogenation/hydrogenation metal is platinum.

13. The process of claim 12, wherein the platinum is intrazeolitic.

14. The process of claim 8, wherein the contacting is undertaken for a period of time which can range from 0.5 to 24 hours or more.

* * * * *